United States Patent [19]

Ferreira

[11] Patent Number: 4,923,403
[45] Date of Patent: May 8, 1990

[54] MICROBIOLOGICAL PROCESS FOR DEGRADATION OF STEROIDS

[75] Inventor: Nicolaas P. Ferreira, Pretoria, South Africa

[73] Assignee: South African Inventions Development Corp., Pretoria, South Africa

[21] Appl. No.: 766,126

[22] Filed: Aug. 15, 1985

[30] Foreign Application Priority Data

Aug. 16, 1984 [ZA] South Africa .................. 84/6385

[51] Int. Cl.⁵ .................. C12P 17/06; C12N 25/00; C12N 1/20; C12R 1/01
[52] U.S. Cl. .................. 435/125; 435/172.1; 435/822; 435/52
[58] Field of Search .............. 435/52, 149, 125, 252.1, 435/148, 141, 169, 822, 172.1

[56] References Cited

U.S. PATENT DOCUMENTS

| | | | |
|---|---|---|---|
| 3,684,657 | 8/1972 | Kraychy et al. | 435/52 |
| 4,097,335 | 6/1978 | Pyke | 435/125 |
| 4,255,344 | 3/1981 | Imada et al. | 260/397.1 |
| 4,304,860 | 12/1981 | Knight et al. | 435/125 |
| 4,784,953 | 11/1988 | Schindler et al. | 435/125 |

FOREIGN PATENT DOCUMENTS

0061687 10/1982 European Pat. Off. .

OTHER PUBLICATIONS

Ferreira et al., "The Microbial Production of 3aα-H--4α-(3'propionic Acid)-5α-Hydroxy-7aβ-Methylhexahydro-Indan-1-one-α-Lactone from Cholesterol", Biotech. Lett., vol. 6, No. 8, pp. 517-522, 1984.
Sneath et al., Bergey's Manual of Systematic Bacteriology, vol. 2, 1986, Williams and Wilkins.
ATCC Catalog, 1985, 16th Ed.
Ferreira et al., J. of Appl. Bact. 57, pp. 429-446, 1984.
IFO Catalogue, 7th Edition, 1984, p. 90.
Goodfellow et al., J. of Gen. Microbiol., 100, pp. 99-122, 1977.
C A Abstract, vol. 97, No. 21, #180151j.
C A Abstract, vol. 94, No. 1, #14025q.
Biotechnology Letters, vol. 6: 517-522.
Ferreira, et al., "Microbial Production . . . ".
Turfitt, G. E. (1948), Biochem. J. 42, 376.
Sih, C. J., Wang, K. C. and Tai, H. H. (1968), Biochemistry 7, 796.
Sih, C. J., Tai, H. H., Tsong, Y. Y., Lee, S. S. and Coombe, R. G. (1968), biochemistry 7, 808.
Tak, J. D. (1942), Antonie van Leuwenhoek, J. Microbiol. Serol., 8, 32.
Schomer, U., Sheldrick, M. S. and Wagner, F. (1978), J.C.S. Perkin 1, 336-340.

(List continued on next page.)

Primary Examiner—Charles F. Warren
Assistant Examiner—Irene Marx
Attorney, Agent, or Firm—Ladas & Parry

[57] ABSTRACT

A process for preparing 3aα-H-4α-[3'-propionic acid]-5α-hydroxy-7aβ-methyl-hexahydro-1-indanone-δ-lactone, having the formula

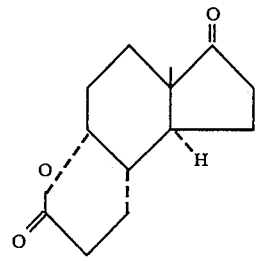

for the chemical synthesis of a pharmaceutical steroid, which includes cultivating, in the presence of cholesterol, sitosterol, stigmasterol, or a mixture of sitosterol and sitostanol, a mutant of the parent species R. australis of the genus Rhodococcus.

8 Claims, 2 Drawing Sheets

OTHER PUBLICATIONS

Schomer, U. and Wagner, F. (1980), European JU. Appl. Microbiol. Biotechnol. 10, 99–106.

Sih, C. J., Wang, K. C. and Tai, H. H. (1967a), J. Am. Chem. Soc., 89, 1956–1957.

Goodfellow, et al., Journal of General Microbiology (1977), vol. 100, 99–122.

Goodfellow, et al., Journal of General Microbiology (1982), vol. 128, 731–745.

Goodfellow, et al., Journal of Applied Bacteriology (1982), vol. 53, 199–207.

Goodfellow, Journal of General Microbiology (1971), vol. 69, 33–80.

Mahato, et al., Phytochemistry 23 (10), Nov. 1984, pp. 2131–2154.

Mahato, et al., Phytochemistry 24 (7), Jul. 1985, pp. 1403–1421.

Kimball, R. F., DNA Repair and Mutagenesis in Eukaryotes, 1980, pp. 1–23.

Chemical Abstracts, vol. 94, No. 1, Jan. 5th, 1981, p. 306, Abstract Number 14925q.

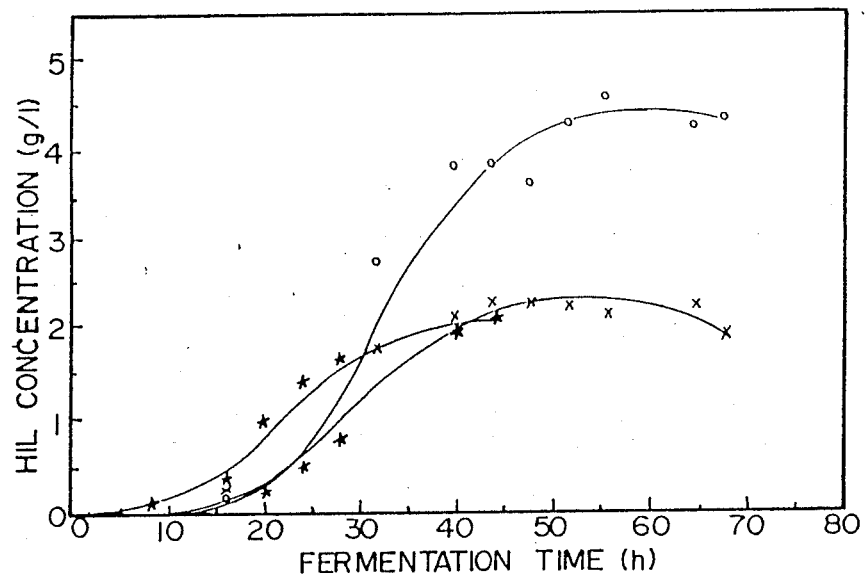
FIG 1  x-x 6   o-o 12   *-* 15
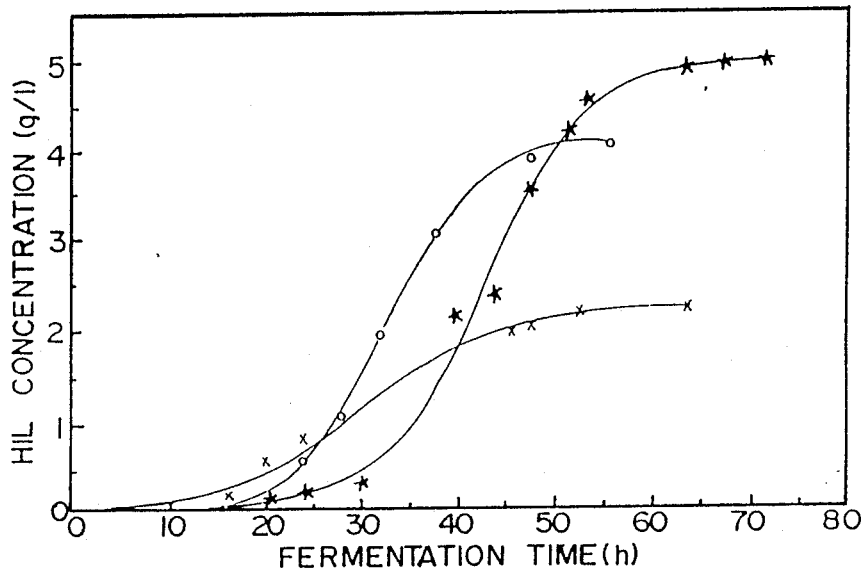
FIG 2  x-x 6   o-o 12   *-* 15

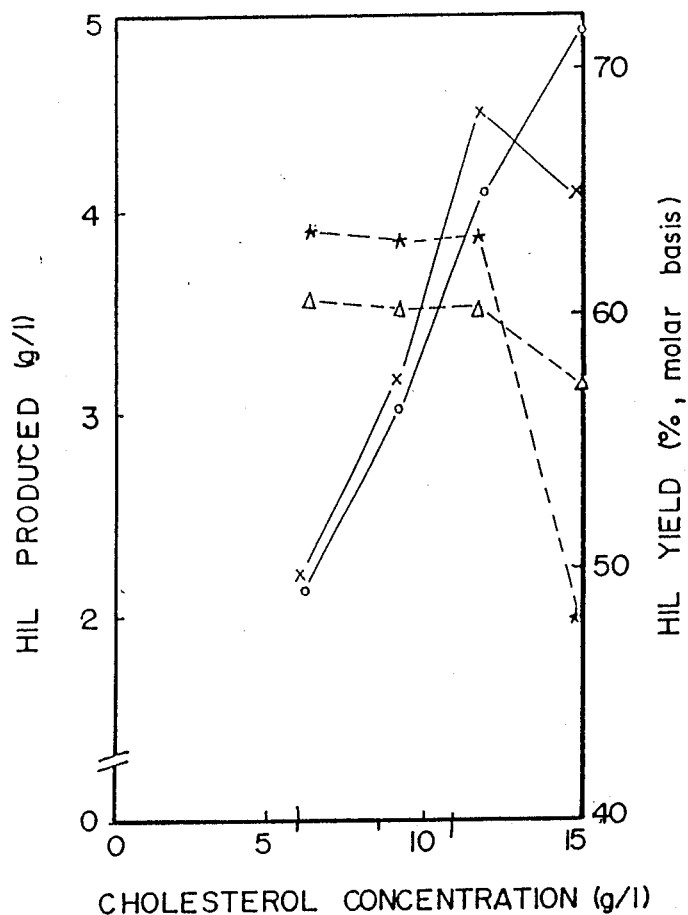
FIG 3  x———x HIL produced (g/ℓ) medium A
x-----x HIL yield (%, molar basis) medium A
o———o HIL produced (g/ℓ) medium B
△-----△ HIL yield (%, molar basis) medium B

MICROBIOLOGICAL PROCESS FOR DEGRADATION OF STEROIDS

This invention relates to the microbiological degradation of steroids.

According to the invention there is provided a process for preparing a steroidal precursor for the chemical synthesis of a pharmaceutical steroid, which includes cultivating, in the presence of a degradable steroid, a micro-organism which can selectively degrade the degradable steroid and accumulate the said steroidal precursor the microorganism being a *Rhodococcus autralis* mutant selected from the group consisting of those mutants identified at the NCIB as NCIB 12146, NCIB 12145, NCIB 12147, and NCIB 12150.

NCIB is a recognized abbreviation for THE NATIONAL COLLECTIONS OF INDUSTRIAL BACTERIA at Torry Research Station, 135 Abbey Road, Aberdeen, Scotland. The steroidal precursor is 3a$\alpha$-H-4$\alpha$-[3'-propionic acid]-5$\alpha$-hydroxy-7a$\beta$-methyl-hexahydro-1-indanone-$\delta$-lactone, having the formula

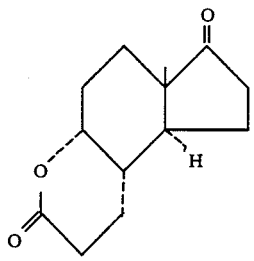

(referred to hereinafter as "HIL").

The micro-organism is of a recently described species which was assigned to the genus Rhodococcus on the basis of its morphological and chemotaxonomic properties as well as the DNA base composition. Both physiological and biochemical properties differ significantly from the other Rhodococcus strains of which the Applicant is aware. The specific name *Rhodococcus australis* is used for this species and is used hereinafter to refer to it.

*Rhodococcus australis* is characterized by the following which is a species description according to the international code for the nomenclature of bacteria: on glucose yeast extract agar the pleomorphic rods soon differentiate into coccal forms. Colonies are white and usually rough. Smooth variants occur. In broth cultures a wrinkled pellicle is formed. The broth remains clear. Growth occurs at 10° C. and 40° C. Urease, phosphatase positive. Neither adenine or tyrosine is degraded. Strains utilize glucose, fructose, mannose, sucrose, trehalose, raffinose, glucosamine and proline, but not glycerol, asparagine, citric acid, oxoglutaric acid, succinic acid, malic acid, fumaric acid, lactic acid, benzoic acid, catechol protocatechuic acid, 3-hydroxy benzoic acid or 2,5-dihydroxy benzoic acid. Acid is produced from glucose, mannose, sucrose and trehalose. Growth occurs on serine, D-glucosamine and l-glutamine. The organisms contain mycolic acid. The guanine plus cytosine content of the DNA is 67.8% by thermal denaturation.

The mutant micro-organism may be cultivated in an aqueous nutrient medium under aerobic conditions in the presence of the degradable steroid. In particular, the nutrient medium may comprise molasses.

The degradable steroid is selected from the group consisting of cholesterol, $\beta$-sitostanol, stigmasterol, and a mixture of any two or more thereof.

The process may include
adding a nitrogen source to a suitable aqueous solution to form a basal medium;
dispersing the degradable steroid in the basal medium to provide a fermentation medium;
inoculating the fermentation medium with the micro-organism to provide a fermentation broth; and
incubating the micro-organism in the fermentation broth, to provide the steroidal precursor.

The steroidal precursor may be isolated from the fermentation broth by solvent extraction. Instead, the steroidal precursor may be isolated from the fermentation broth by adsorption on a suitable ion exchange column, followed by elution of the steroidal precursor therefrom.

The concentration of the degradable steroid in the fermentation medium may be between 0.2 g/l and 100.0 g/l, preferably between 0.2 g/l and 15.0 g/l, and more preferably about 2 g/l.

The concentration of nitrogen in the fermentation medium may be between 20 mg/l and 1000 mg/l, preferably about 250 to 400 mg/l.

The process according to the invention may include as a preliminary step, the step of preparing the mutant micro-organism from its parent strain by mutagenesis with N-methyl-N'-nitro-N-nitrosoguanidine. This may be achieved by the method described by Adelberg, E. A., Mandel, M., and Chen, G. C. C. (1965) in Biochem. Biophys. Res. Comm. 18, 788–795.

The invention is now described by way of the following non-limiting examples:

Two parent strains of a species of the genus Rhodococcus (which species is herein referred to as *Rhodococcus australis*) were isolated from soil using conventional microbiological techniques. The parent micro-organisms were assigned to the genus Rhodococcus on the basis of their morphological and chemotaxonomic properties as well as their DNA base composition and are identified in the NCIB as NCIB 12142 and NCIB 12143 respectively.

Three different mutant strains were prepared from the parent NCIB 12143 and one mutant strain was prepared from the parent NCIB 12142 by mutagenesis with N-methyl-N'-nitro-N-nitrosoguanidine according to the method described by Adelberg, E. A., Mandel, M., and Chen, G. C. C. (1965) in Biochem. Biophys. Res. Comm. 18, 788–795. The parent strain of mutant NCIB 12150 is the micro-organism identified at the NCIB as NCIB 12142, and the parent strain of mutants NCIB 12145, NCIB 12146 and NCIB 12147 is the micro-organism identified at the NCIB as NCIB 12143.

The mutants of strain NCIB 12143 which are identified in the NCIB as NCIB 12146, NCIB 12145, and NCIB 12147, respectively and the mutant of strain NCIB 12142 which is identified in the NCIB as NCIB 12150 were routinely maintained on slants of PY agar which included peptone, yeast extract and agar in distilled water in concentrations of 5 g/l, 3 g/l and 5 g/l respectively.

EXAMPLE 1

A basal medium comprising a salt solution (see Stanier, R. Y., Palleroni, N.J. and Doudoroff, M. (1966) Journal of General Microbiology, 43, 159–271) supplemented with 4 g/l of acid hydrolyzed soy protein was employed.

Cholesterol was selected as a suitable degradable steroid for degradation by the said four mutant microorganisms.

A suspension of cholesterol in Tween 80 solution (ICI America Incorporated) was prepared by appropriately mixing together cholesterol and a 2.0% (v/v) Tween 80 solution to provide a 2.0% (v/v) concentration of cholesterol. A predetermined volume of the said suspension of cholesterol in Tween 80 solution was added to the basal medium to provide a fermentation medium having a concentration of 2 g/l of cholesterol and 2 g/l of Tween 80.

Each of ten 500 ml Erlenmeyer flasks was charged with 100 ml of the fermentation medium and inoculated with mutant NCIB 12145 directly from an appropriate slant to provide a fermentation broth.

The flasks containing the fermentation broths were shaken on a reciprocal shaker at 120 cycles/minute at 30° C. for 6 days.

After the incubation period the fermentation broths were clarified by centrifugation. 500 ml of the clarified broth was acidified to pH 2 with sulphuric acid and extracted with an equal volume of a water immiscible solvent, e.g. chloroform. The extract was concentrated in vacuo and the concentrated extract, 5.5 g, was subjected to preparative thin layer chromatograpy on silica gel plates (E. Merck Darmstadt) using a solvent system of chloroform:ether 80:20 v/v. A fermentation product was obtained and was visualized by spraying the plates with cerium sulphate in 50% sulphuric acid and heating the sprayed plates at 120° C. The fermentation product appeared as a purple spot rf. 0.25. The fermentation product was eluted from the silica gel with chloroform concentrated in vacuo and re-crystallised from methanol. The remaining 500 ml of the fermentation broths were subjected to column chromatography on amberlite XAD-2 (BDH Chemicals Ltd, Poole, England) and eluted with a water gradient with an increasing content of methanol and 5% methylene chloride. Fractions containing the fermentation product were identified by thin layer chromatography as described above, and evaporated to dryness in vacuo. The product (0.42 g) was re-crystallised from methanol. The resulting crystalline products from both isolation methods were found to be characterized by the following data: m.p. (MeOH) 121°–122° C.; $|\alpha|_D^{25} +121°$; $^1$H-NMR: 0.91 (s, 18-H$_3$) and 4.50 (1H, q, J=2.5 H$_z$, 5$\beta$- H); $\eta_{max}$ 1745 cm$^{-1}$; $^{13}$C-NMR 218 (C-1), 171.41, 77.74 (C-5), 47.35 (C-7a), 41.67 (C-3a), 35.15 (C-2), 32.39, 26.54, 26.36, 21.28, 20.94, 12.63 (C - 7a$\beta$), m/e, 222 (M+).

These data are characteristic of the lactone HIL, and no other degradation product was detected.

EXAMPLE 2

Each of four 100 ml Erlenmeyer flasks was charged with 20 ml of the fermentation medium. A first thereof was inoculated with mutant NCIB 12146, a second with mutant NCIB 12145, a third with mutant NCIB 12150, and a fourth with mutant NCIB 12147 directly from the appropriate slants, to form four different fermentation broths.

The four flasks containing the fermentation broths were shaken on a reciprocal shaker at 120 cycles/minute at 30° C. to produce fermentation steroid degradation product compounds.

The respective concentrations of cholesterol and HIL present in each of the fermentation broths at the end of the six day incubation period were determined with a Perkin-Elmer Sigma 3 gas chromatograph equipped with a glass column (2.0 mm ID×1.0 M) packed with 3% OV17 (Supelco Incorporated) on CHROMOSORB G (80–100 mesh) (John Manville, Celite Division) and operating at 245° C. with a nitrogen flow rate of 25 ml/min. 5- α- cholestane was employed as an internal standard.

The relative concentrations of HIL are given below in Table 1.

TABLE 1

Concentration of HIL produced by various mutants of R. australis in shake flasks after a 6-day incubation period.

| MUTANT NO. | CONCENTRATION HIL g/l | HIL MOL % YIELD |
| --- | --- | --- |
| NCIB 12146 | 0.844 | 76.8 |
| NCIB 12145 | 0.883 | 74.8 |
| NCIB 12150 | 0.765 | 66.5 |
| NCIB 12147 | 0.647 | 56.3 |

EXAMPLE 3

Example 2 was repeated except that (a) a further six 100 ml Erlenmeyer flasks were used instead of the four of example 2;

(b) in the second, third, fourth, fifth and sixth flasks, cholesterol was replaced by equivalent concentrations of $\beta$- sitosterol, stigmasterol, ergosterol, cholic acid and deoxycholic acid respectively; and (c) all of the six flasks were inoculated with the mutant NCIB 12145.

After the six day incubation period, chemical analysis identified the degradation product in each of the first, second and third flasks/fermentation broths to be HIL, and no other degradation product was detected.

The concentration of HIL present in each of the fermentation broths at the end of the six day incubation period is given below in Table 2.

TABLE 2

Concentration of HIL produced from various above-specified sterols by R. australis NCIB 12145 in shake flasks after a 6-day incubation period.

| DEGRADABLE STEROID | CONCENTRATION HIL g/l | HIL MOL % YIELD |
| --- | --- | --- |
| Cholesterol | 0.886 | 76.8 |
| $\beta$-sitosterol | 0.765 | 66.5 |
| stigmasterol | 0.883 | 74.8 |
| ergosterol | 0 | 0 |
| cholic acid | 0 | 0 |
| deoxycholic acid | 0 | 0 |

EXAMPLE 4

Two fermentation solutions, namely solution A and solution B were prepared.

Fermentation solution A included the following components in distilled water:

| COMPONENT | CONCENTRATION IN g/l OF DISTILLED WATER. |
| --- | --- |
| yeast extract | 2.000 |
| acid hydrolyzed soy protein | 4.000 |
| dipotassium hydrogen phosphate (K$_2$HPO$_4$) | 1.200 |
| ammonium nitrate (NH$_4$NO$_3$) | 1.200 |

-continued

| COMPONENT | CONCENTRATION IN g/l OF DISTILLED WATER. |
|---|---|
| calcium chloride ($CaCl_2.2H_2O$) | 0.240 |
| magnesium sulphate ($MgSO_4.7H_2O$) | 0.040 |
| ferrous sulphate ($FeSO_4.7H_2O$) | 0.012 |
| glucose | 4.000 | and was prepared by mixing all of the components, except glucose, together and thereafter sterilizing the resulting solution. The glucose was sterilized separately and added aseptically to the said sterile solution.

Fermentation solution B included the following components in distilled water:

| COMPONENT | CONCENTRATION IN g/l OF DISTILLED WATER |
|---|---|
| cane sugar molasses | 26.4 |
| ammonium nitrate ($NH_4NO_3$) | 1.2 |

A suspension of cholesterol in Tween 80 solution was prepared by appropriately mixing together 30 g of cholesterol and 500 ml of Tween 80 solution containing 0.4 g Tween 80. This suspension was sterilized and added aseptically to both solutions A and B respectively to provide a fermentation medium A and a fermentation medium B, each with a cholesterol concentration of 6 g/l.

An inoculum of the mutant strain NCIB 12145 was prepared by inoculating 20 ml PY medium (i.e. a distilled water solution of peptone and yeast extract in concentrations of 5 g/l and 3 g/l respectively) from an appropriate slant. After shaking at 30° C. for 48 hours on a reciprocal shaker at 120 cycles per minute, 10 ml of the resulting inoculum were used to inoculate 500 ml of fermentation medium A and 500 ml of fermentation medium B respectively in 1 liter aspirator bottles. The fermentation media A and B were then incubated on an orbital shaker at 150 revolutions per minute and 30° C. for 24 hours. Thereafter the entire contents of each of the aspirator bottles was transferred to a 7 liter "Chemap PEC" glass fermentor vessel under aseptic conditions. The contents of each of the fermentor vessels were made up to a volume of 5 liters with distilled water to provide a fermentation broth A and a fermentation broth B respectively. These broths were then permitted to ferment for forty eight hours.

Both at the start and at the end of the forty eight hour fermentation period, glucose and sucrose concentrations in the fermentation broths A and B were measured with Boehringer Mannheim GOD - period blood glucose and sucrose-glucose-fructose analytical kits respectively.

The pH values of the fermentation broth in the fermentor vessels were maintained at 7.5 with 4N sodium hydroxide, and Dow Corning Silicone DB31 (of Dow Corning Africa Silicone Incorporated) was used as an antifoam, added to the broth when required by means of a conventional automatic foam controller. The fermentation broths were agitated at a constant rate of 600 rpm and maintained at 30° C. Further, the fermentation broths were aerated at a rate of 3 /min of air, and an overpressure of 1 kg/cm was maintained in the fermentor vessel throughout the fermentation period.

A sample of each of the fermentation broths A and B was taken from the fermentors after 24, 32, 40 and 48 hours.

Each of the samples was weighed and acidified to pH 2 with sulphuric acid. The cholesterol and HIL components were extracted therefrom with chloroform, and the HIL was purified from the final crude extract by recrystallization from methanol.

Chemical analysis identified the degradation product in each sample to be HIL and no other degradation product was detected.

The concentration of cholesterol and HIL present in each sample was determined by chromatographic analysis as described above for Example 1.

The yield of HIL on a % molar basis was calculated in respect of each sample.

The fermentations which were characterized by a relatively long lag phase were very similar in both fermentation media A and B. HIL product formation commenced after 16 to 20 hours in fermentation broth A, and after 20 to 24 hours in fermentation broth B.

EXAMPLE 5

Example 4 was repeated except that
(a) the concentration of cholesterol in each of the fermentation media A and B was raised from 6 g/l to 12 g/l; and
(b) a further sample was taken from fermentation broth B after 72 hours and chemically and chromatographicaly analysed.

EXAMPLE 6

Example 5 was repeated except that the concentration of cholesterol in each of the fermentation media A and B was raised from 12 g/l to 15 g/l.

The results of Examples 4, 5 and 6, i.e. the relative concentrations of HIL produced after various fermentation times for media A and B, are given in Tables 3 and 4 respectively and are represented graphically in FIGS. 1 and 2 respectively. FIG. 1 shows HIL production in Medium A at various cholesterol concentrations (g/l). FIG. 2 shows HIL production in Medium B at various cholesterol concentrations (g/l).

Further, the concentrations of HIL in the last sample taken and analysed from each of the media A and B in each of Examples 4 to 6 appear in Table 5 below to illustrate the effect of cholesterol concentration on HIL product concentration. The yield of HIL was calculated for each said last sample and these values are also given in Table 5 and are represented graphically in FIG. 3 below. FIG. 3 shows effect of cholesterol concentration on HIL production by *R. australis*.

EXAMPLE 7

Example 4 was repeated except that
(a) the concentration of cholesterol in each of the media A and B was raised from 6 g/l to 9 g/l; and
(b) only one sample was taken from each of media A and B and analysed, the sample of media being taken after 48 hours and the sample of media B being taken after 72 hours.

The relative concentrations of HIL produced and the relative yields thereof on a % molar basis are given below in Table 5 and represented graphically in FIG. 3.

TABLE 3

Concentration of HIL produced for various concentrations of cholesterol at various time intervals after start of fermentation in medium A.

| Time Interval in hours | Concentraton of HIL (g/l) | | |
|---|---|---|---|
| | Cholesterol = 6 g/l | Cholesterol = 12 g/l | Cholesterol = 15 g/l |
| 24 | 0.497 | 0.267 | 0.763 |
| 32 | 1.72 | 2.73 | 2.04 |
| 40 | 2.08 | — | — |
| 48 | 2.20 | 3.84 | 2.81 |
| 72 | — | 4.30 | 3.55 |

TABLE 4

Concentration of HIL produced for various concentrations of cholesterol at various time intervals after start of fermentation in medium B.

| Time Interval in hours | Concentraton of HIL (g/l) | | |
|---|---|---|---|
| | Cholesterol = 6 g/l | Cholesterol = 12 g/l | Cholesterol = 15 g/l |
| 24 | 0.837 | 0.59 | 0.22 |
| 32 | — | 1.94 | 0.34 |
| 40 | 0.964 | 3.03 | 2.13 |
| 48 | 2.15 | 3.87 | 3.50 |
| 72 | — | 4.09 | 4.81 |

TABLE 5

Concentration of HIL produced from various cholesterol concentrations after various incubation periods.

| | Medium A | | | | Medium B | | | |
|---|---|---|---|---|---|---|---|---|
| Cholesterol conc (g/l) | 6 | 9 | 12 | 15 | 6 | 9 | 12 | 15 |
| Fermentation period (hours) | 48 | 72 | 72 | 72 | 48 | 72 | 72 | 72 |
| HIL conc. (g/l) | 2.20 | 3.15 | 4.30 | 3.55 | 2.15 | 3.20 | 4.09 | 4.81 |
| HIL yield (% mol) | 62.30 | 60.00 | 62.00 | 48.00 | 62.0 | 61.0 | 62.4 | 55.8 |

As mentioned above, the rates of HIL product formation in media A and B are illustrated graphically in FIGS. 1 and 2, and the effect of the cholesterol concentration on the transformation efficiency of the mutant NCIB 12145 is illustrated graphically in FIG. 3.

From the said analyses of the fermentation broths A and B at successive time intervals, it was found that the available cholesterol was completely assimilated in a 60-hour fermentation period in medium A and a 72-hour fermentation period in medium B, which can clearly be seen from FIGS. 1 and 2 to correspond with maximum HIL product formation.

It is also evident from FIGS. 1 and 2 that the HIL product was not extensively degraded after the cholesterol was assimilated, and in fact it was found that HIL was not significantly degraded at all by the said mutant over a 3-day incubation period.

It was found further as is illustrated graphically in FIG. 3, that the conversion efficiency of the said mutant at the higher level of concentration of cholesterol (i.e. 15 g/l) was significantly lower in both medium A and medium B than at the cholesterol concentration levels in the range of 6 g/l to 12 g/l.

EXAMPLE 8

Example 7 was repeated except that cholesterol was added incrementally, in order to ascertain whether the inhibitory effect of the higher cholesterol level could thus be reduced. However, incremental addition of the cholesterol inhibited HIL product formation completely.

The degradable steroids used in the preceding example were chemically pure. The following examples were carried out with crude, commercial grade sitosterols.

EXAMPLE 9

Two identical fermentation solutions were prepared. Each of the fermentation solutions included the following components in distilled water:

| COMPONENT | CONCENTRATION IN g/l OF DISTILLED WATER |
|---|---|
| yeast extract | 2.000 |
| acid hydrolyzed soy protein | 4.000 |
| dipotassium hydrogen phosphate (K$_2$HPO$_4$) | 1.200 |
| ammonium nitrate (NH$_4$NO$_3$) | 1.200 |
| calcium chloride (CaCl$_2$.2H$_2$O) | 0.240 |
| magnesium sulphate (MgSO$_4$.7H$_2$O) | 0.040 |
| ferrous sulphate (FeSO$_4$.7H$_2$O) | 0.012 |
| glucose | 4.000 | and were prepared by mixing all of the components, except glucose, together and thereafter sterilising the resulting solution. The glucose was sterilised separately and added aseptically to the said sterile solution.

Two different mixtures comprising crude, commercial grade degradable steroid constitutents α-sitosterol, β-sitostanol and β-sitosterol were prepared. The mixtures are hereinafter referred to as "TYPE U" and "TYPE P" mixtures respectively. The compositions of the mixtures are given in Table 6 below.

TABLE 6

Composition of the mixtures TYPE U and TYPE P, each having an approximate sterol content of about 90% m/m of the mixture.

| Constituent | Degradable steroid mixtures - (proportions in % m/m of total) | |
|---|---|---|
| | TYPE U | TYPE P |
| α-sitosterol | 76% | 52% |
| β-sitostanol | 14% | 13% |
| β-sitosterol | 0.1% | 25% |

A suspension of mixture TYPE U in Tween 80 solution was prepared by appropriately mixing together 190 g of mixture TYPE U and 3 l of a Tween 80 solution containing 0.2 g Tween 80. This suspension was sterilized and added aseptically to one of the fermentation solutions to provide a TYPE U fermentation medium with a TYPE U mixture concentration of approx 12.5 g/l. Similarly, a suspension of mixture TYPE P in Tween 80 solution was prepared by appropriately mixing together 190 g of mixture TYPE P and 3 l of a Tween 80 solution containing 0.2 g Tween 80. This suspension was sterilized and added aseptically to the other fermentation solution to provide a TYPE P fermentation medium with a TYPE P mixture concentration of approx 12.5 g/l.

An inoculum of the mutant strain NCIB 12145 was prepared by inoculating 20 ml PY medium (ie a distilled water solution of peptone and yeast extract in concentrations of 5 g/l and 3 g/l respectively) from an appropriate slant. After shaking at 30° C. for 48 hours on a reciprocal shaker at 120 cycles per minute, 10 ml of the resulting inoculum were used to inoculate 500 ml of TYPE U fermentation medium and 500 ml of TYPE P fermentation medium respectively in 1 liter aspirator bottles. The fermentation media TYPE U and TYPE P were then incubated on an orbital shaker at 150 revolutions per minute and 30° C. for 24 hours. Thereafter the entire contents of each of the aspirator bottles was transferred to a 20 liter "Chemap PEC" glass fermentor vessel under aseptic conditions. The contents of each of the fermentor vessels were made up to a volume of 15 liters with distilled water to provide a TYPE U fermentation broth and a TYPE P fermentation broth respectively.

Both at the start and at the end of the fermentation period, the glucose concentration in the TYPE U and TYPE P fermentation broths were measured as described in Example 4.

The pH values of the fermentation broth in the fermentor vessels were maintained at pH 7.5 with 4N sodium hydroxide, and Dow Corning Silicone DB31 (of Dow Corning Africa Silicone Incorporated) was used as an antifoam, added to the broth when required by means of a conventional automatic foam controller. The fermentation broths were agitated at a constant rate of 800 rpm and maintained at 30° C. Further, the fermentation broths were aerated at a rate of 3 l/min of air, and an overpressure of 1 kg/cm was maintained in the fermentor vessels throughout the fermentation period.

A sample of about 200 g of each of the TYPE U and TYPE P fermentation broths was taken from the fermentors after 0, 24, 48, 72 and 96 hours.

Each of the samples was weighed and adjusted to pH 8 with sodium hydroxide. Residual steroids were extracted from the samples with chloroform. The samples were then acidified to pH 2 with sulphuric acid and the HIL components of the samples were extracted therefrom with chloroform. The HIL was purified from the final crude extract by re-crystallization from methanol.

Chemical analysis identified the degradation product in each sample to be HIL and no other degradation product was detected.

The concentrations of cholesterol and HIL present in each sample were determined by chromatographic analysis as described above for Example 1.

The fermentations, which were characterised by a relatively long lag phase, were very similar for both TYPE U and TYPE P broths. HIL product formation occurred after 16 to 20 hours in TYPE U fermentation broth, and in TYPE P fermentation broth.

As mentioned above, both at the start and at the end of the four day fermentation period, glucose concentrations in the TYPE U and TYPE P fermentation broths were measured. In both broths, approximately 50% of the glucose was not utilized during the incubation period.

TABLE 7

Concentration of HIL produced from mixtures of degradable steroids, viz TYPE U mixture and TYPE P mixture at various time intervals after start of fermentation.

| Time Interval in hours | Concentration of HIL (mg/l) | |
|---|---|---|
| | TYPE U Mixture | TYPE P Mixture |
| 0 | 0.00 | 0.00 |
| 24 | 0.63 | 0.68 |
| 48 | 1.22 | 1.29 |
| 72 | 2.18 | 1.78 |
| 96 | 2.47 | 1.92 |

The molar conversion efficiencies of the TYPE U and TYPE P mixtures were calculated, firstly as percentages of the total mixtures and then as percentages of the β-sitosterol constituents. The percentages are given in TABLE 8 below.

TABLE 8

Molar conversion efficiency of TYPE U and TYPE P mixtures to HIL

| Mixture of degradable steroids | Molar conversion based on mixture % m/m | Molar conversion based on sterol constituent % m/m |
|---|---|---|
| TYPE U | 27.5 | 36 |
| TYPE P | 21.0 | 41 |

Advantages of the invention, at least as exemplified, include the efficiency with which the degradable steroid is transformed and the resultant good volume-time yield, even for crude, commercial grade steroids. The rate of degradable steroid utilization and the conversion efficiency of the mutant is relatively high. Further, the HIL product formed according to the process of the invention is not significantly degraded at all before the degradable steroid is exhausted. Yet a further advantage of the mutant of the invention is that the degradable steroid is also transformed to HIL in high yield in a simple molasses medium, which is of major importance to the development of an economic biotechnological process.

The micro-organisms specified herein as microorganisms NCIB 12142, NCIB 12143, NCIB 12150, NCIB 12145, NCIB 12146, NCIB 12147, were deposited in the National Collections of Industrial Bacteria (i.e. the NCIB) at Torry Research Station, 135 Abbey Road, Aberdeen, Scotland on Aug. 13, 1985.

I claim:

1. A process for preparing a steroidal precursor for the chemical synthesis of a pharmaceutical steroid, which comprises cultivating, in the presence of a degradable steroid, a micro-organism which can selectively degrade the degradable steroid and accumulate the steroidal precursor, the micro-organism being a *Rhodococcus australis* mutant selected form the group consisting of those mutants identified at the NCIB 12146, NCIB 12145, NCIB 12150 and NCIB 12147, the degradable steroid being a steroid selected from the group consisting of cholesterol, β-sitosterol, stigmasterol and a mixture of any two or more thereof, and the steroidal precursor being 3aα-H-4α-[3'-propionic acid]-5α-hydroxy-7aβ-methyl-hexahydro-1-indanone-δ-lactone, having the formula:

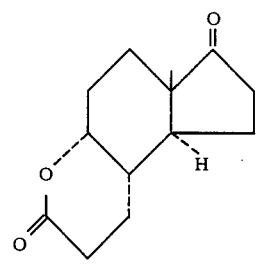

2. A process as claimed in claim 1, which includes cultivating the micro-organism in an aqueous nutrient medium under aerobic conditions.

3. A process as claimed in claim 1, which includes adding a nitrogen source to a suitable aqueous solution to form a basal medium;
dispersing the degradable steroid in the basal medium to provide a fermentation medium;
inoculating the fermentation medium with the micro-organism to provide a fermentation broth; and
incubating the micro-organism in the fermentation broth to provide the steroidal precursor.

4. A process as claimed in claim 3, which includes isolating the steroidal precursor from the fermentation broth by solvent extraction.

5. A process as claimed in claim 3, which includes isolating the steroidal precursor from the fermentation broth by adsorption on a suitable ion exchange column, followed by elution of the steroidal precursor therefrom.

6. A process as claimed in claim 3, wherein the concentration of the degradable steroid in the fermentation medium is from 0.2 g/l to 15.0 g/l.

7. A process as claimed in claim 3, wherein the concentration of nitrogen in the fermentation medium is about 250 to 400 mg/l.

8. A process as claimed in claim 1, which includes a preliminary step of preparing the mutant micro-organism from its parent strain which is NCIB 12142 or NCIB 12143, by mutagenesis with N-methyl-N'-nitro-N-nitrosoguanidine.

* * * * *